US010501415B2

(12) United States Patent
Fukubayashi et al.

(10) Patent No.: US 10,501,415 B2
(45) Date of Patent: Dec. 10, 2019

(54) METHOD FOR PRODUCING BISIMIDE DICARBOXYLIC ACID

(71) Applicant: UNITAKA LTD., Amagasaki-shi, Hyogo (JP)

(72) Inventors: Yumeto Fukubayashi, Uji (JP); Makoto Nakai, Uji (JP); Akira Shigeta, Uji (JP); Munenori Yamada, Uji (JP)

(73) Assignee: UNITIKA LTD., Amagasaki-Shi, Hyogo (JP)

(*) Notice: Subject to any disclaimer, the term of this patent is extended or adjusted under 35 U.S.C. 154(b) by 0 days.

(21) Appl. No.: 15/564,667

(22) PCT Filed: Apr. 6, 2016

(86) PCT No.: PCT/JP2016/061291
§ 371 (c)(1),
(2) Date: Oct. 5, 2017

(87) PCT Pub. No.: WO2016/163412
PCT Pub. Date: Oct. 13, 2016

(65) Prior Publication Data
US 2018/0086704 A1   Mar. 29, 2018

(30) Foreign Application Priority Data
Apr. 7, 2015 (JP) ................. 2015-078792

(51) Int. Cl.
*C07D 209/48* (2006.01)
*B01J 19/00* (2006.01)
*C07B 43/06* (2006.01)
*C07D 403/10* (2006.01)

(52) U.S. Cl.
CPC ........ *C07D 209/48* (2013.01); *B01J 19/0013* (2013.01); *C07B 43/06* (2013.01); *C07D 403/10* (2013.01)

(58) Field of Classification Search
CPC .................................................. C07D 209/48
See application file for complete search history.

(56) References Cited

U.S. PATENT DOCUMENTS

| | | |
|---|---|---|
| 4,066,631 A | 1/1978 | Dimmig |
| 4,291,149 A | 9/1981 | Keske et al. |
| 4,861,862 A | 8/1989 | Tyrell et al. |
| 5,587,452 A | 12/1996 | Koning et al. |
| 5,939,520 A | 8/1999 | Langsam |

FOREIGN PATENT DOCUMENTS

| | | | |
|---|---|---|---|
| FR | 2399452 A1 | | 3/1979 |
| GB | 1116379 | * | 7/1964 |
| JP | 42-15637 B | | 8/1967 |
| JP | 44-19274 B | | 8/1969 |
| JP | 45-2397 B | | 1/1970 |
| JP | 49-4077 B | | 1/1974 |
| JP | 50-33120 B | | 10/1975 |
| JP | 55-120628 A | | 9/1980 |
| JP | 56-501883 A | | 12/1981 |
| JP | 62-39629 A | | 2/1987 |
| JP | 63-117035 A | | 5/1988 |
| JP | 8-48775 A | | 2/1996 |
| JP | 8-59614 A | | 3/1996 |
| JP | 11-128703 A | | 5/1999 |
| JP | 2001-122858 A | | 5/2001 |
| JP | 2007-119395 A | | 5/2007 |
| WO | WO 81/02016 A1 | | 7/1981 |
| WO | WO 2011/121850 A1 | | 10/2011 |

OTHER PUBLICATIONS

M-Xylylenediamine data sheet, obtained from ChemSpider on Sep. 12, 2018, p. 1-4. (Year: 2018).*
Trimetllitic anhydride data sheet, obtained from ChemSpider on Sep. 12, 2018, p. 1-4. (Year: 2018).*
Ammonia aqueous solution, retrieved from GESTIS Substance database, http://gestis-en.itrust.de/nxt/gateway.dll/gestis_en/001750.xml?f=templates$fn=default.htm$3.0 (Year: 2019).*
International Search Report for PCT/JP2016/061291 dated Jul. 5, 2016.
Extended European Search Report for European Application No. 16776578.3, dated Dec. 5, 2017.
International Preliminary Report on Patentability and English translation of the Written Opinion of the International Searching Authority issued in the corresponding International Application No. PCT/JP2016/061291 dated Oct. 19, 2017.
English translation of the International Search Report (form PCT/ISA/210), dated Jul. 12, 2016, for International Application No. PCT/JP2016/061297.
International Preliminary Report on Patentability and English translation of the Written Opinion of the International Searching Authority (forms PCT/IB/373, PCT/ISA/237 and PCT/IB/338), dated Oct. 19, 2017, for International Application No. PCT/JP2016/061297.
European Patent Office Communication and extended search report issued in the European Patent Application No. 16776583.3 dated Mar. 21, 2018.
U.S. Appl. No. 15/564,678, filed Oct. 5, 2017.

(Continued)

*Primary Examiner* — Karen Cheng
(74) *Attorney, Agent, or Firm* — Birch, Stewart, Kolasch & Birch, LLP

(57) ABSTRACT

An object of the present invention is to provide an industrially advantageous method for producing a bisimide dicarboxylic acid, which uses substantially no solvent and requires no granulation after completion of the reaction.
The above object can be achieved by a method for producing a bisimide dicarboxylic acid with a tricarboxylic acid anhydride and a diamine, including the following processes (i) and (ii):
a process (i) in which, provided that a compound having a higher melting point is a high melting compound and a compound having a lower melting point is a low melting compound, when a melting point is compared between the tricarboxylic acid anhydride and the diamine, the high melting compound is heated at a temperature between less than the melting point of the high melting compound and not lower than the melting point of the low melting compound, and the low melting compound is added to the high melting compound while the high melting compound maintains its solid states, to give a mixture; and
a process (ii) in which the resultant mixture in the process (i) is heated while its solid states are kept, to give bisimide dicarboxylic acid.

3 Claims, No Drawings

(56) References Cited

OTHER PUBLICATIONS

Taiwanese Office Action and Search Report dated May 15, 2019 for Application No. 105110738 with an English translation of the Office Action.
Taiwanese Office Action and Search Report dated May 15, 2019 for Application No. 105110739 with an English translation of the Office Action.
Chinese Search Report and Office Action, dated Jul. 3, 2019, for Chinese Application No. 201680020195.3, with a partial English translation of the Chinese Search Report.

* cited by examiner ically applicable method for producing a bisimide dicarboxylic acid.

METHOD FOR PRODUCING BISIMIDE DICARBOXYLIC ACID

TECHNICAL FIELD

The present invention relates to a method for producing a bisimide dicarboxylic acid.

BACKGROUND ART

A bisimide dicarboxylic acid made from a tricarboxylic acid anhydride and a diamine is industrially useful as a dicarboxylic acid raw material for polymers such as polyamide-imide and polyesterimide.

As a method for producing a bisimide dicarboxylic acid, there has been known a method in which a tricarboxylic acid anhydride and a diamine are reacted in a solvent (such as aliphatic carboxylic acids, N,N-dialkylcarboxyamides, alcohols, esters, and halogenated hydrocarbons). However, since the reaction is carried out in a solvent in the above method, it is necessary to separate and purify the bisimide dicarboxylic acid from the reaction solution after completion of the reaction in order to use the resulting bisimide dicarboxylic acid as a polymer raw material. Thus, it takes much time and energy.

Patent Document 1 discloses a method for mixing and reacting an aromatic tricarboxylic acid anhydride and a diamine. However, although the method of Patent Document 1 does not require separation and purification after completion of the reaction, mixing by an extruder, a kneader or the like is carried out, so that the resulting bisimide dicarboxylic acid is obtained in bulk. In order to use the bisimide dicarboxylic acid as a polymer raw material, the bisimide dicarboxylic acid should be granulated by pulverization, classification or the like. Thus, it takes much time and energy.

PRIOR ART DOCUMENT

Patent Documents

Patent Document 1: Japanese Patent Laid-Open Publication No. 8-59614

SUMMARY OF INVENTION

Technical Problems

An object of the present invention is to provide an industrially advantageous method for producing a bisimide dicarboxylic acid, which uses substantially no solvent and requires no granulation after completion of the reaction.

Solutions to Problems

As a result of intensive studies to solve the above problems, the present inventors have reached the present invention.

That is, the gist of the present invention is as follows.

A method for producing a bisimide dicarboxylic acid with a tricarboxylic acid anhydride and a diamine, including the following processes (i) and (ii):

a process (i) in which, provided that a compound having a higher melting point is a high melting compound and a compound having a lower melting point is a low melting compound, when a melting point is compared between the tricarboxylic acid anhydride and the diamine, the high melting compound is heated at a temperature between less than the melting point of the high melting compound and not lower than the melting point of the low melting compound, and the low melting compound is added to the high melting compound while the high melting compound maintains its solid states, to give a mixture; and a process (ii) in which the resultant mixture in the process (i) is heated while its solid states are kept, to give bisimide dicarboxylic acid.

Effects of Invention

The present invention can provide an industrially advantageous method for producing a bisimide dicarboxylic acid, which uses substantially no solvent and requires no granulation after completion of the reaction.

In addition, according to the present invention, the purity of bisimide dicarboxylic acid is very high.

DESCRIPTION OF EMBODIMENTS

A tricarboxylic acid anhydride used in the present invention is an aromatic tricarboxylic acid anhydride or alicyclic tricarboxylic acid anhydride. Examples of a ring of tricarboxylic acid include a benzene ring, a naphthalene ring, an anthracene ring, a biphenyl ring, a cyclohexane ring, preferably a benzene ring, a naphthalene ring, a biphenyl ring, a cyclohexane ring, more preferably a benzene ring, a cyclohexane ring, still more preferably a benzene ring.

Tricarboxylic acid includes those in which a hydrogen atom bonding to a ring is replaced by another atom or an atomic group.

Specific examples of the tricarboxylic acid anhydride include trimellitic acid anhydride, 2,3,6-naphthalene tricarboxylic acid anhydride, 2,3,6-anthracene tricarboxylic acid anhydride, 3,4,4'-biphenyl tricarboxylic acid anhydride, 1,2,4-cyclohexane tricarboxylic acid anhydride and the like, preferably trimellitic acid anhydride, 2,3,6-naphthalene tricarboxylic acid anhydride, 3,4,4'-biphenyl tricarboxylic acid anhydride, 1,2,4-cyclohexane tricarboxylic acid anhydride, more preferably trimellitic acid anhydride, or 1,2,4-cyclohexane tricarboxylic acid anhydride, still more preferably trimellitic acid anhydride.

The tricarboxylic acid anhydride may be used singly or in combination of two or more kinds.

The diamine used in the present invention is an aliphatic diamine, an alicyclic diamine, or an aromatic diamine. Preferably, the diamine is an aliphatic diamine or an aromatic diamine. The diamine may contain —O— and —S—, and one or more hydrogen atoms may be replaced by halogen or may have a side chain.

Specific examples of the diamine include hexamethylenediamine, heptamethylenediamine, octamethylenediamine, nonamethylenediamine, decamethylenediamine, m-phenylenediamine, p-phenylenediamine, m-xylylenediamine, p-xylylenediamine, benzidine, 4,4'-diaminodiphenylpropane, 4,4'-diaminodiphenylmethane, 4,4'-diaminodiphenyl sulfide, 3,3'-diaminodiphenyl sulfone, 4,4'-diaminodiphenyl ether, 1,5-diaminonaphthalene, 3,3-diaminonaphthalene, 1,4-diaminocyclohexane, 1,10-diamino-1,10-dimethyldecane, and 1,4-bis (aminomethyl) cyclohexane.

Preferred examples include m-phenylenediamine, p-phenylenediamine, m-xylylenediamine, p-xylylenediamine, 4,4'-diaminodiphenyl ether, benzidine, more preferably m-phenylenediamine, p-phenylenediamine, m-xylylenediamine, p-xylylenediamine, 4,4'-diaminodiphenyl ether, still more preferably an aliphatic diamine selected from m-xylylenediamine and p-xylylenediamine, or an aromatic diamine selected from p-phenylenediamine and 4,4'-diaminodiphenyl ether.

These diamines may be used singly or in combination of two or more kinds.

The production method of the present invention includes the following processes (i) and (ii).

Process (i): a process in which, provided that a compound having a higher melting point is a high melting compound and a compound having a lower melting point is a low melting compound, when a melting point is compared between the tricarboxylic acid anhydride and the diamine, the high melting compound is heated at a temperature between less than the melting point of the high melting compound and not lower than the melting point of the low melting compound, and the low melting compound is added to the high melting compound while the high melting compound maintains its solid states, to give a mixture.

Process (ii): a process in which the resultant mixture in the process (i) is heated while its solid states are kept, to give bisimide dicarboxylic acid.

The process (i) is a process in which the tricarboxylic acid anhydride and the diamine are mixed or reacted with each other to give a mixture. The mixture contains unreacted tricarboxylic acid, unreacted tricarboxylic acid anhydride, unreacted diamine, amic acid produced by reacting tricarboxylic acid anhydride and diamine in a molar ratio of 1:1 or 2:1, and furthermore, the amic acid partially or entirely imidized, and the like.

In the process (i), the step in which "the high melting compound maintains its solid states" during the process can be achieved by reacting a liquid low melting compound with a solid high melting compound. Specifically, this step can be achieved by heating the high melting compound at a temperature between less than the melting point of the high melting compound and not lower than the melting point of the low melting compound and adding the low melting compound at an appropriate rate.

The heating temperature is preferably in a temperature range lower by 5 to 10° C. or more than the melting point of the high melting compound, and heating is carried out in a temperature range higher by 5 to 10° C. or more than the melting point of the low melting compound in order to prevent as much as possible the influence on a difference in melting rate caused by heat absorption due to melting, difference in thermal conductivity depending on size and shape, and the like. The specific heating temperature is appropriately selected based on a combination of the high melting compound and the low melting compound based on the above criteria. The "melting point" in the process (i) is also called "a fusing point" and is used in the general meaning of the temperature at which a solid melts. The melting point can be determined by heating a sample filled in a capillary and visually observing the melting point, or by means of a measuring apparatus such as differential scanning calorimetry (DSC).

In the process (i), when the reaction is carried out at a temperature equal to or higher than the melting point of the high melting compound, the high melting compound melts, the content becomes a form of a melt or slurry, and after completion of the reaction in the process (ii), a bisimide dicarboxylic acid is obtained in bulk, which is not preferable. On the other hand, when the reaction is carried out at a temperature less than the melting point of the low melting compound, it is not preferable because the high melting compound and the low melting compound do not react. When the mixture is heated in the process (ii), the total amount of the low melting compound simultaneously melts, the content becomes the form of a melt or slurry, and after completion of the reaction, a bisimide dicarboxylic acid is obtained in bulk, which is not preferable.

In order to allow the high melting compound to maintain its solid state, it is preferable to use substantially no solvent or substantially no dispersion medium, and it is more preferable not to use them at all.

The low melting compound is not particularly limited as long as it is in a liquid state with respect to the solid high melting compound at the time of reaction, and may be in a liquid state or a solid state (powdery or particulate state) when added.

While the high melting compound may be heated after the addition of the low melting compound or before the addition of the low melting compound, the latter is more preferable.

The process (i) is preferably carried out under an inert atmosphere such as a nitrogen atmosphere.

From the viewpoint of maintaining stably the conditions of being in its solid state of the high melting compound, the addition rate of the low melting compound in the process (i) is preferably from 0.005 to 2.00% by mass/min, more preferably from 0.01 to 1.00% by mass/min. Here, "% by mass/min" means the ratio of the amount of the low melting compound added in 1 minute to the total amount of the low melting compound added eventually.

The process (ii) is a process in which the mixture obtained in the process (i) is reacted to give bisimide dicarboxylic acid. In the process (ii), in order to keep the solid states of the mixture during the process, in addition to the temperature condition of the process (i), the heating temperature may be set to be less than the melting point of the bisimide dicarboxylic acid, which is an intended product, and preferably may be set to be lower by 5 to 10° C. or more than its melting point.

The process (ii) is also preferably carried out under an inert atmosphere such as a nitrogen atmosphere.

The apparatus used in the process (i) is not particularly limited as long as mixing can be carried out at a temperature equal to or higher than the melting point of the low melting compound, and a known polymerization apparatus can be used. When the low melting compound is a liquid at room temperature, an apparatus not equipped with a heating function may be used.

The apparatus used in the process (ii) is not particularly limited as long as mixing can be carried out at a temperature equal to or higher than the temperature in the reaction for removal of water from tricarboxylic acid, and a known polymerization apparatus can be used. Above all, a heating and stirring apparatus with a vent capable of distilling off water of a reaction product is more preferable.

The bisimide dicarboxylic acid obtained by the production method of the present invention can be suitably used as a raw material of polyamide-imide or polyesterimide.

EXAMPLES

Hereinafter, the present invention will be specifically described based on examples. However, the present invention is not limited to these examples.

(1) Purity and Mass Measurement of Bisimide Dicarboxylic Acid

The purity was measured by a high-performance liquid chromatograph-mass spectrometer (LC/MS) under the following conditions.

Sample: bisimide dicarboxylic acid/DMSO solution (200 µg/mL)

Apparatus: microTOF2-kp made by Bruker Daltonics K.K.

Column: Cadenza CD-C18 3 μm 2 mm×150 mm

Mobile phase: (mobile phase A) 0.1% formic acid aqueous solution, (mobile phase B) methanol Gradient (B Conc.): 0 min (50%)-5, 7 min (60%)-14.2 min (60%)-17 min (100%)-21.6 min (100%)-27.2 min (50%)-34 min (50%)

Ionization method: ESI

Detection condition: Negative mode

The purity meant the proportion occupied by imide dicarboxylic acid among all the components contained in the obtained sample, and was obtained by the proportion occupied by an imide dicarboxylic acid component among the ion intensity ratios of all the components detected in the mass spectrum obtained by mass spectrometry.

(2) Identification of Bisimide Dicarboxylic Acid

Measurement was carried out by a nuclear magnetic resonance (NMR) and infrared spectroscopy (IR) under the following conditions, and identification was made.

Nuclear magnetic resonance (NMR)

Apparatus: JNM-ECA 500 made by JEOL Ltd.

Measurement nuclide: proton

Solvent: deuterated dimethylsulfoxide

Temperature: 25° C.

Number of times of integrations: 128

Infrared spectroscopy (IR)

Apparatus: System 2000 infrared spectrometer made by PerkinElmer Co., Ltd.

Method: KBr method

Number of times of integrations: 64 scans (resolution 4 $cm^{-1}$)

Example 1

Particulate trimellitic anhydride (738 parts by mass) (melting point: 168° C.) was added to a mixing tank equipped with a double helical type stirring blade, and heated to 80° C. under a nitrogen atmosphere while stirring. While confirming that the shape of trimellitic anhydride was maintained, m-xylylenediamine (262 parts by mass) (melting point: 14° C.) heated to 80° C. was added thereto at a rate of 0.66 parts by mass/min (0.252% by mass/min) by using a liquid sending device to give a mixture. During and after addition, the contents were particulate.

Thereafter, while the mixture was stirred, the temperature was raised to 300° C. and heating was carried out at 300° C. for 2 hours.

The obtained main component bisimide dicarboxylic acid (the following structure) was particulate and the purity was 98.2%.

[Chemical Formula 1]

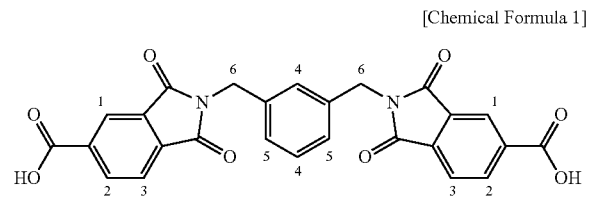 [SMILES: O=C(O)c1ccc2c(c1)C(=O)N(Cc1cccc(CN3C(=O)c4ccc(C(=O)O)cc4C3=O)c1)C2=O]

Since absorption could be confirmed near 1778 $cm^{-1}$ and 1714 $cm^{-1}$ by IR measurement, formation of an imide bond was confirmed. In the NMR measurement, peaks derived from the main component were detected near 8.34 ppm (doublet) (attributed peak structure: 2), 8.20 ppm (singlet) (attributed peak structure: 1), 7.95 ppm (doublet) (attributed peak structure: 3), 7.27 ppm (triplet, singlet) (attributed peak structure: 4), 7.20 ppm (doublet) (attributed peak structure: 5), and 4.75 ppm (singlet) (attributed peak structure: 6) in 1H-NMR spectrum. From the result of mass spectrometry, the molecular weight of the main component was estimated to be 484 (m/z).

Example 2

Particulate trimellitic anhydride (738 parts by mass) (melting point: 168° C.) was added to a mixing tank equipped with a double helical type stirring blade, and heated to 80° C. under a nitrogen atmosphere while stirring. While confirming that the shape of trimellitic anhydride was maintained, solid p-xylylenediamine (262 parts by mass) (melting point: 60 to 63° C.) was added thereto at a rate of 1.32 parts by mass/min (0.504% by mass/min) by using a powder sending device equipped with a double damper mechanism to give a mixture. During and after addition, the contents were particulate.

Thereafter, while the mixture was stirred, the temperature was raised to 300° C. and heating was carried out at 300° C. for 2 hours.

The obtained main component bisimide dicarboxylic acid (the following structure) was particulate and the purity was 98.8%.

[Chemical Formula 2]

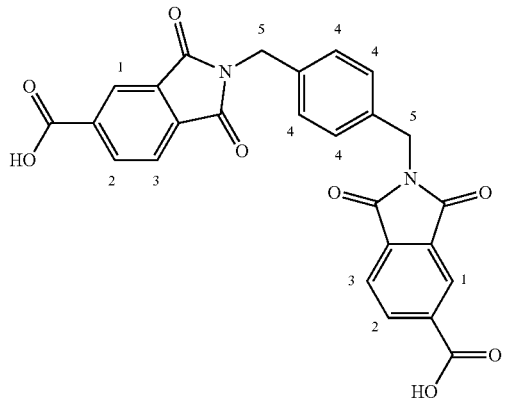

Since absorption could be confirmed near 1778 $cm^{-1}$ and 1714 $cm^{-1}$ by IR measurement, formation of an imide bond was confirmed. In the NMR measurement, peaks derived from the main component were detected near 8.34 ppm (doublet) (attributed peak structure: 2), 8.20 ppm (singlet) (attributed peak structure: 1), 7.97 ppm (doublet) (attributed peak structure: 3), 7.27 ppm (singlet) (attributed peak structure: 4), and 4.74 ppm (singlet) (attributed peak structure: 5) in 1H-NMR spectrum. From the result of mass spectrometry, the molecular weight of the main component was estimated to be 484 (m/z).

Example 3

Particulate trimellitic anhydride (780 parts by mass) (melting point: 168° C.) was added to a mixing tank equipped with a double helical type stirring blade, and heated to 150° C. under a nitrogen atmosphere while stirring. While confirming that the shape of trimellitic anhydride was maintained, solid p-phenylenediamine (220 parts by mass) (melting point: 139° C.) was added thereto at a rate of 1.32 parts by mass/min (0.600% by mass/min) by using a powder sending device equipped with a double damper mechanism to give a mixture. During and after addition, the contents were particulate.

Thereafter, while the mixture was stirred, the temperature was raised to 300° C. and hearing was carried out at 300° C. for 2 hours.

The obtained main component bisimide dicarboxylic acid (the following structure) was particulate and the purity was 98.6%.

[Chemical Formula 3]

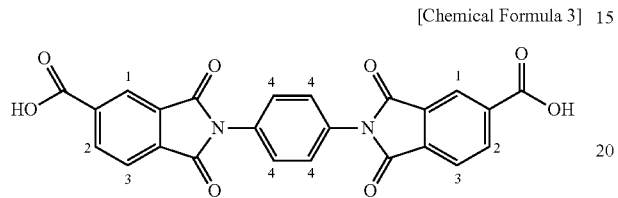

Since absorption could be confirmed near 1778 cm$^{-1}$ and 1714 cm$^{-1}$ by IR measurement, formation of an imide bond was confirmed. In the NMR measurement, peaks derived from the main component were detected near 8.43 ppm (doublet) (attributed peak structure: 2), 8.33 ppm (singlet) (attributed peak structure: 1), 8.10 ppm (doublet) (attributed peak structure: 3), and 7.63 ppm (singlet) (attributed peak structure: 4) in 1H-NMR spectrum. From the result of mass spectrometry, the molecular weight of the main component was estimated to be 456 (m/z).

Example 4

Particulate 4,4'-diaminodiphenyl ether (343 parts by mass) (melting point: 188 to 192° C.) was added to a mixing tank equipped with a double helical type stirring blade, and heated to 175° C. under a nitrogen atmosphere while stirring. While confirming that the shape of 4,4'-diaminodiphenyl ether was maintained, solid trimellitic anhydride (657 parts by mass) (melting point: 168° C.) was added thereto at a rate of 2.64 parts by mass/min (0.402% by mass/min) by using a powder sending device equipped with a double damper mechanism to give a mixture. During and after addition, the contents were particulate.

Thereafter, while the mixture was stirred, the temperature was raised to 300° C. and heating was carried out at 300° C. for 2 hours.

The obtained main component bisimide dicarboxylic acid (the following structure) was particulate and the purity was 98.0%.

was confirmed. In the NMR measurement, peaks derived from the main component were detected near 8.41 ppm (doublet) (attributed peak structure: 2), 8.30 ppm (singlet) (attributed peak structure: 1), 8.08 ppm (doublet) (attributed peak structure: 3), 7.51 ppm (doublet) (attributed peak structure: 4), and 7.24 ppm (doublet) (attributed peak structure: 5) in 1H-NMR spectrum. From the result of mass spectrometry, the molecular weight of the main component was estimated to be 548 (m/z).

Example 5

Particulate cyclohexane-1,2,4,-tricarboxylic acid-1,2-anhydride (744 parts by mass) (melting point: 155° C.) was added to a mixing tank equipped with a double helical type stirring blade, and heated to 80° C. under a nitrogen atmosphere while stirring. While confirming that the shape of cyclohexane-1,2,4-tricarboxylic acid-1,2-anhydride was maintained, m-xylylenediamine (256 parts by mass) (melting point: 14° C.) heated to 80° C. was added thereto at a rate of 0.66 parts by mass/min (0.252% by mass/min) by using a liquid sending device to give a mixture. During and after addition, the contents were particulate.

Thereafter, while the mixture was stirred, the temperature was raised to 300° C. heating was carried out at 300° C. for 2 hours.

The obtained main component bisimide dicarboxylic acid (the following structure) was particulate and the purity was 98.6%.

[Chemical Formula 5]

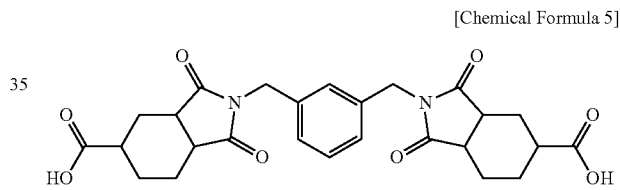

Since absorption could be confirmed near 1778 cm$^{-1}$ and 1714 cm$^{-1}$ by IR measurement, formation of an imide bond was confirmed. In the NMR measurement, the peaks overlapped in a complicated manner, and attribution was difficult. However, in mass spectrometry, the main component could be quantitatively separated, so that it was estimated that the molecular weight of the main component was 496 (m/z).

Comparative Example 1

Particulate trimellitic anhydride (638 parts by mass) (melting point: 168° C.) was added to a mixing tank

[Chemical Formula 4]

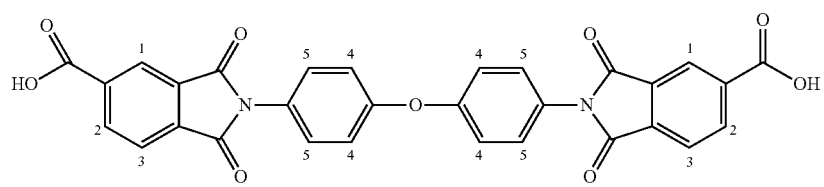

Since absorption could be confirmed near 1778 cm$^{-1}$ and 1714 cm$^{-1}$ by IR measurement, formation of an imide bond equipped with a double helical type stirring blade, and heated to 200° C. under a nitrogen atmosphere while stirring. When trimellitic anhydride melted, m-xylylenediamine (262 parts by mass) (melting point: 14° C.) heated to 80° C. was added at a rate of 0.66 parts by mass/min (0.252% by mass/min) by using a liquid sending device to give a mixture. During addition, the contents changed into a melt or slurry.

Thereafter, the mixture was heated to 300° C. and heating was carried out at 300° C. for 2 hours.

The obtained bisimide dicarboxylic acid was in bulky state and the purity was 80.2%.

Comparative Example 2

Particulate trimellitic anhydride (638 parts by mass) (melting point: 168° C.) was added to a mixing tank equipped with a double helical type stirring blade, and heated to 25° C. under a nitrogen atmosphere while stirring. While confirming that the shape of trimellitic anhydride was maintained, p-xylylenediamine (262 parts by mass) (melting point: 60 to 63° C.) heated to 80° C. was added thereto at a rate of 1.32 parts by mass/min (0.504% by mass/min) by using a liquid sending device to give a mixture of trimellitic anhydride and p-xylylenediamine. During addition, the contents changed into a bulky state.

Thereafter, the mixture was heated to 300° C. and heating was carried out 300° C. for 2 hours.

The obtained bisimide dicarboxylic acid was in a bulky state and the purity was 78.8%.

All of Examples 1 to 4 were industrially advantageous production methods, using substantially no solvent and requiring no granulation after completion of the reaction. In all of Examples 1 to 4, the purity was very high.

The invention claimed is:

1. A method for producing a bisimide dicarboxylic acid with a tricarboxylic acid anhydride and a diamine, where said tricarboxylic acid anhydride is an aromatic tricarboxylic acid anhydride, an alicyclic tricarboxylic acid anhydride, or a mixture thereof and wherein said diamine is an aliphatic diamine, an alicyclic diamine, an aromatic diamine, or a mixture thereof, the method comprising the following processes (i) and (ii):

a process (i) in which, provided that a compound having a higher melting point is a high melting compound and a compound having a lower melting point is a low melting compound, when a melting point is compared between the tricarboxylic acid anhydride and the diamine, the high melting compound is heated at a temperature between less than the melting point of the high melting compound and not lower than the melting point of the low melting compound, and the low melting compound is added, in a melted state, at a temperature in a range lower by 5 to 10° C. or more than the ng point of the high melting compound and at a temperature in a range higher by 5 to 10° C. or more than the melting point of the low melting compound and at an addition rate from 0.005 to 2.00% by mass/ minute to the high melting compound, while the high melting compound maintains its solid state, to give a mixture; and a process (ii) in which the resultant mixture in the process (i) is heated while the solid state of the high melting compound is kept, and the melted state of the low melting compound is kept; to give bisimide dicarboxylic acid.

2. A method of claim 1, wherein the solid state is particulate.

3. A method of claim 1, wherein the low melting compound is added in a powdery state or a particulate state in the process (i), and wherein the resultant mixture in the process (i) is heated at a temperature between less than the melting point of the high melting compound and not lower than the melting point of the low melting compound while the solid state of the high melting compound is kept, and the low melting compound is kept in a melted state, to give bisimide dicarboxylic acid.

* * * * *

UNITED STATES PATENT AND TRADEMARK OFFICE
CERTIFICATE OF CORRECTION

PATENT NO. : 10,501,415 B2
APPLICATION NO. : 15/564667
DATED : December 10, 2019
INVENTOR(S) : Yumeto Fukubayashi et al.

Page 1 of 1

It is certified that error appears in the above-identified patent and that said Letters Patent is hereby corrected as shown below:

On the Title Page

Item [71], change "UNITAKA LTD." to --UNITIKA LTD.--

Signed and Sealed this
Twenty-fifth Day of February, 2020

Andrei Iancu
*Director of the United States Patent and Trademark Office*